US00PP33986P2

(12) United States Plant Patent
Masor

(10) Patent No.: US PP33,986 P2
(45) Date of Patent: Mar. 1, 2022

(54) ***ANGELONIA* PLANT NAMED 'BALADANIOB'**

(50) Latin Name: *Angelonia angustifolia*
Varietal Denomination: Baladaniob

(71) Applicant: Ball Horticultural Company, West Chicago, IL (US)

(72) Inventor: Laura L. Masor, Grover Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/501,560

(22) Filed: Oct. 14, 2021

(51) Int. Cl.
*A01H 6/68* (2018.01)
*A01H 5/02* (2018.01)

(52) U.S. Cl.
USPC ..... Plt./404

(58) Field of Classification Search
USPC ..... Plt./404
See application file for complete search history.

*Primary Examiner* — Annette H Para
(74) *Attorney, Agent, or Firm* — Audrey Charles

(57) ABSTRACT

A new and distinct cultivar of *Angelonia* plant named 'Baladaniob', characterized by its deep violet and white bicolored flowers, dark green-colored foliage, and moderately vigorous, upright growth habit, is disclosed.

1 Drawing Sheet

Latin name of genus and species of plant claimed: *Angelonia angustifolia.*
Variety denomination: 'Baladaniob'.

BACKGROUND OF THE INVENTION

The present invention relates to a new and distinct cultivar of *Angelonia* plant botanically known as *Angelonia angustifolia* and hereinafter referred to by the cultivar name 'Baladaniob'.

The new cultivar originated in a controlled breeding program in Arroyo Grande, Calif. during August 2016. The objective of the breeding program was the development of *Angelonia* cultivars having large flowers, unique flower coloration, and an upright growth habit.

The new *Angelonia* cultivar is the result of cross-pollination. The female (seed) parent of the new cultivar is the proprietary *Angelonia angustifolia* breeding selection coded LM6990-4, not patented, characterized by its dark purple and white bicolored flowers, dark green-colored foliage, and vigorous, upright growth habit. The male (pollen) parent of the new cultivar is the proprietary *Angelonia angustifolia* breeding selection coded LM7087-1, not patented, characterized by its medium purple and lime bicolored flowers, medium green-colored foliage, and moderately vigorous, upright growth habit. The new cultivar was discovered and selected as a single flowering plant within the progeny of the above stated cross-pollination during May 2017 in a controlled environment in Arroyo Grande, Calif.

Asexual reproduction of the new cultivar by terminal stem cuttings since May 2017 in Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Baladaniob' as a new and distinct cultivar of *Angelonia* plant:

1. Deep violet and white bicolored flowers;
2. Dark green-colored foliage; and
3. Moderately vigorous, upright growth habit.

Plants of the new cultivar differ from plants of the female parent primarily in having a slightly different shade of flower color and in having reduced growth vigor. Plants of the new cultivar differ from plants of the male parent primarily in flower color and in having violet and white bicolored flowers and a darker green foliage color.

Of the many commercially available *Angelonia* cultivars, the most similar in comparison to the new cultivar is Archangel Blue Bicolor 'Balarclubi', not patented. However, in side-by-side comparisons, plants of the new cultivar differ from plants of 'Balarclubi' in at least the following characteristics:

1. Plants of the new cultivar are taller than plants of 'Balarclubi';
2. Plants of the new cultivar have a deep violet and white bicolored flower color unlike plants of 'Balarclubi'; and
3. Plants of the new cultivar have a more pronounced white flower color than plants of 'Balarclubi'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Baladaniob'. The plants were approximately 4.5-months old. The plants were grown in 3-gallon containers for approximately 11 weeks in an outdoor nursery in West Chicago, Ill. Plants were pinched twice prior to transplant.

DETAILED BOTANICAL DESCRIPTION

Figure 1:
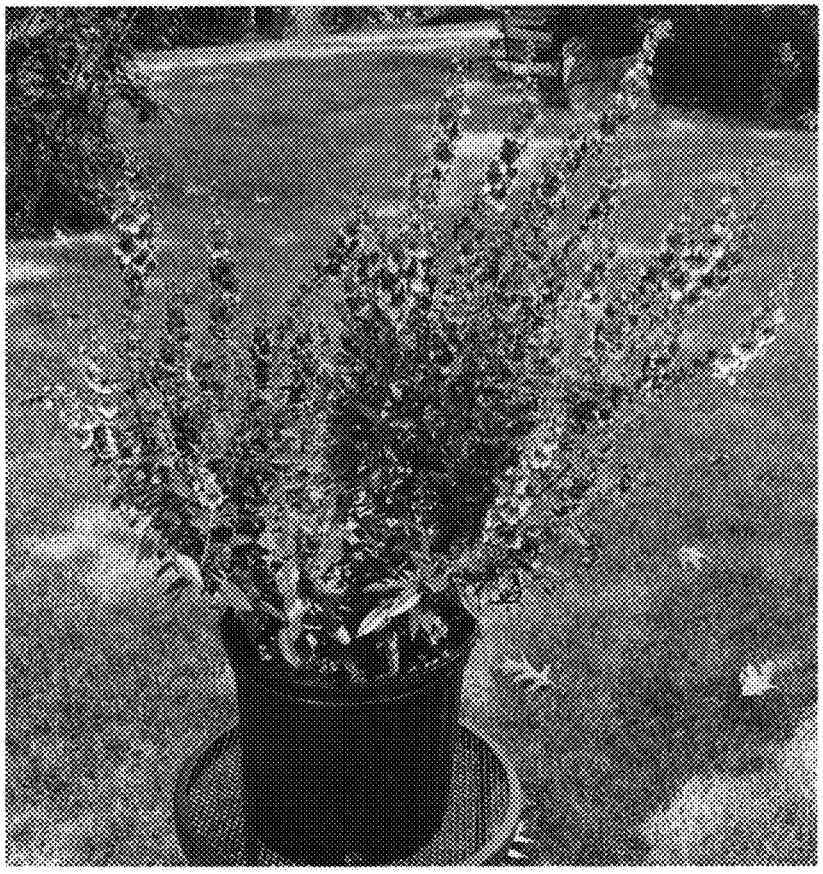
FIG. 1 illustrates a side view of the overall growth and flowering habit of 'Baladaniob'.
Figure 2:
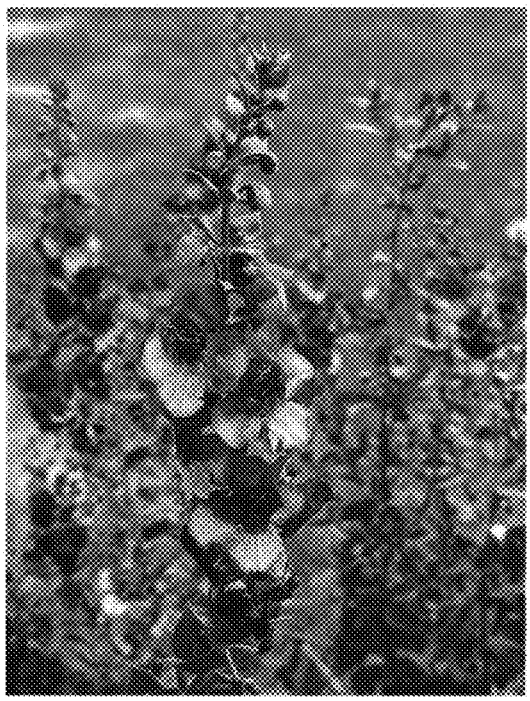
FIG. 2 illustrates a close-up view of an individual inflorescence of 'Baladaniob'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in August 2021 under natural light conditions in Naperville, Ill.

The following descriptions and measurements describe approximately 4.5-month-old plants produced from cuttings from stock plants and grown under conditions comparable to those used in commercial practice. The plants were grown in 3-gallon containers for approximately 11 weeks in an outdoor nursery in West Chicago, Ill. Plants were given two pinches prior to transplant. Prior to transplant plants were grown in a polycarbonate greenhouse in West Chicago, Ill. Greenhouse temperatures were maintained at approximately 70° F. to 85° F. (21° C. to 29° C.) during the day and approximately 60° F. to 70° F. (16° C. to 21° C.) during the night. Supplemental lighting was used during propagation stage. Measurements and numerical values represent averages of typical plants.

Botanical classification: *Angelonia angustifolia* 'Baladaniob'.

Parentage:

*Female parent.*—Proprietary *Angelonia angustifolia* breeding selection coded LM6990-4, not patented.

*Male parent.*—Proprietary *Angelonia angustifolia* breeding selection coded LM7087-1, not patented.

Propagation:

*Type cutting.*—Terminal stem.

*Time to initiate roots.*—Approximately 7 to 9 days.

*Time to produce a rooted cutting.*—Approximately 21 to 28 days.

*Root description.*—Fine, fibrous.

*Rooting habit.*—Freely branching.

Plant description:

*Commercial crop time.*—Approximately 5 to 8 weeks from a rooted cutting to finish in a 10 cm pot.

*Growth habit and general appearance.*—Moderately vigorous, upright.

*Size.*—Height from soil level to top of plant plane: Approximately 68.0 cm. Width: Approximately 64.0 cm.

*Branching habit.*—Freely branching, pinching improves basal branching. Quantity of main branches per plant: Approximately 7.

*Branch.*—Shape: Square in cross section. Strength: Moderately strong. Length: Approximately 45.0 cm. Diameter: Approximately 4.0 mm to 7.0 mm. Length of central internode: Approximately 3.5 cm. Texture: Glabrous. Color of young and mature stems: 144B.

Foliage description:

*General description.*—Quantity of leaves per main branch: Approximately 22. Fragrance: None. Form: Simple. Arrangement: Opposite.

*Leaves.*—Aspect: Primarily perpendicular or obtuse angle to stem. Shape: Elliptic. Margin: Widely serrate. Apex: Acute. Base: Sessile. Venation pattern: Pinnate. Length of mature leaf: Approximately 5.3 cm. Width of mature leaf: Approximately 1.8 cm. Texture of upper and lower surfaces: Sparsely glandular pubescent. Gland color: Colorless, transparent. Color of upper surface of young and mature foliage: NN137A with midvein of 146C and other venation indistinguishable. Color of lower surface of young and mature foliage: Closest to 146A with midvein of 146C and other venation indistinguishable.

Flowering description:

*Flowering habit.*—'Baladaniob' is freely flowering under outdoor growing conditions with substantially continuous blooming from spring through autumn and year-round in greenhouse environment.

*Lastingness of individual flower on the plant.*—Approximately 7 to 10 days.

Inflorescence description:

*General description.*—Type: Terminal raceme. Quantity per plant: Approximately 65. Fragrance: Slight, sweet. Length: Approximately 23.0 cm. Width: Approximately 3.0 cm to 4.0 cm. Quantity of fully open flowers per inflorescence: Approximately 5 to 8.

Flower description:

*Type.*—Solitary, zygomorphic.

*Bud.*—Rate of opening: Generally takes 3 to 4 days for bud to progress from first color to fully open flower.

*Bud just before opening.*—Shape: Globular. Diameter: Approximately 6.0 mm. Color of upper surface: 145B. Color of lower surface: 144A.

*Corolla.*—Shape: Bilabiate. Aspect: Facing outward. Length: Approximately 2.6 cm. Width: Approximately 2.3 cm. Depth: Approximately 8.0 mm.

*Petals.*—Quantity: 5 petals fused at base forming a throat and consisting of an upper lip with 2 petals and a lower lip with 3 petals, consisting of 2 lateral petals and one central petal. Shape: Obovate. Margin: Entire, wavy. Apex: Obtuse.

*Upper lip.*—Length of petals from throat: Approximately 8.0 mm. Width of each petal: Approximately 1.2 cm. Texture of upper surface: Densely glandular pubescent. Gland color: 150C and colorless, transparent. Texture of lower surface: Sparsely glandular pubescent. Gland color: Colorless, transparent. Color of upper surface when fully open: 83B to 83C. Color of lower surface when fully open: 83C to 83D.

*Lower lip, lateral petals.*—Length of petals from throat: Approximately 9.0 mm. Width of each petal: Approximately 1.1 cm. Texture of upper and lower surfaces: Densely glandular pubescent. Gland color: 150C and colorless, transparent. Color of upper surface when fully open: NN155A mottled with 83A, 83B to 83C on approximately one third of area nearest upper petals, margins of 83D adjacent to NN155A. Color of lower surface when fully open: 155A with 83C to 83D on approximately one third of area nearest upper petals, margins of 83D adjacent to 155A.

*Lower lip, central petal.*—Length from the palate: Approximately 9.0 mm. Width: Approximately 1.0 cm. Texture of upper and lower surfaces: Densely glandular pubescent. Gland color: 150C and colorless, transparent. Color of upper surface when fully open: NN155A mottled with 83A and margins of 83D. Color of lower surface when fully open: 155A with margins of 83D.

*Throat.*—Length: Approximately 8.0 mm. Width: Approximately: 7.0 mm. Texture of inner surface: Moderately glandular pubescent. Texture of outer surface: Sparsely glandular pubescent. Gland color: 150C, transparent. Color of inner surface: NN155D with a faint overlay of 83C and 144A and spots of N79A. Color of outer surface: 83D with spots of N79A. Palate color: 144A with spots of N79A and lower lip of NN155D mottled with 83A. Palate texture: Sparsely glandular pubescent. Gland color: 150C, transparent. Teeth color: 144D with 83D.

*Calyx.*—Shape: Star, cupped. Diameter: Approximately 6.0 mm.

*Sepals.*—Quantity per flower: 5, fused at base. Shape: Ovate. Apex: Acute. Length: Approximately 3.0 mm. Width: Approximately 2.0 mm. Texture of upper (inner) surface: Sparsely glandular pubescent. Texture of lower (outer) surface: Densely glandular pubescent. Gland color: 150C and colorless, transparent. Color of upper (inner) surface: 137A. Color of lower (outer) surface: 137A with an overlay of 187A.

*Pedicel.*—Strength: Strong, flexible. Aspect: Acute angle to stem. Length: Approximately 1.3 cm. Diameter: Approximately 1.0 mm. Texture: Sparsely glandular pubescent. Gland color: Colorless, transparent. Color: 146B with a heavy overlay of 187A.

*Reproductive organs.*—Androecium: Stamen quantity: 4 per flower. Filament length: Approximately 4.0 mm. Filament texture: Sparsely glandular pubescent. Gland color: Colorless, transparent. Filament color: NN155D faintly tinted with 83A. Anther shape: Bilobed. Anther length: Approximately 1.0 mm. Anther color: 83A. Pollen amount: Abundant. Pollen color: 155D. Gynoecium: Pistil quantity: 1 per flower. Pistil length: Approximately 4.0 mm. Stigma shape: Pointed. Stigma length: Less than 1.0 mm. Stigma color: NN155D. Style length: Approximately 3.0 mm. Style color: NN155D. Ovary diameter: Approximately 1.0 mm. Ovary texture: Sparsely glandular pubescent. Gland color: 150C, transparent. Ovary color: 146D.

Seed and fruit production: Neither seed nor fruit production has been observed.

Disease and pest resistance: Resistance to pathogens and pests common to *Angelonia* has not been observed.

What is claimed is:

1. A new and distinct cultivar of *Angelonia* plant named 'Baladaniob', substantially as herein illustrated and described.

* * * * *